(12) United States Patent
Rowland et al.

(10) Patent No.: US 9,888,687 B2
(45) Date of Patent: Feb. 13, 2018

(54) **METHODS AND COMPOSITIONS FOR REDUCING *ANGUINA* NEMATODE INFESTATION AND IMPROVING GRASS QUALITY**

(71) Applicant: Bayer CropScience LP, Research Triangle Park, NC (US)

(72) Inventors: John Hudson Rowland, Austin, TX (US); Richard Rees, Chapel Hill, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 15/195,500

(22) Filed: Jun. 28, 2016

(65) Prior Publication Data
US 2017/0006869 A1 Jan. 12, 2017

Related U.S. Application Data

(60) Provisional application No. 62/189,369, filed on Jul. 7, 2015.

(51) Int. Cl.
*A01N 43/40* (2006.01)
(52) U.S. Cl.
CPC .................................. *A01N 43/40* (2013.01)

(58) Field of Classification Search
CPC .............................. A01N 43/40; A01N 25/00
See application file for complete search history.

(56) References Cited

U.S. PATENT DOCUMENTS

| 8,648,101 | B2 | 2/2014 | Suwa | |
|---|---|---|---|---|
| 8,865,622 | B2* | 10/2014 | Andersch | A01N 43/40 504/100 |
| 2010/0249193 | A1 | 9/2010 | Andersch et al. | |
| 2013/0116119 | A1 | 5/2013 | Rees et al. | |
| 2013/0253018 | A1* | 9/2013 | Hungenberg | A01N 43/40 514/357 |
| 2014/0005047 | A1 | 1/2014 | Hungenberg et al. | |
| 2014/0364309 | A1 | 12/2014 | Hellwege et al. | |

OTHER PUBLICATIONS

Giat et al. (J of Nemtology, 40, 252-257, 2008).*
Martinez-Espinoza et al. (http://caes2.caes.uga.edu/commodities/turfgrass/georgiaturf/Publicat/PCRP2017/Nematode%20Control%20in%20Commercial%20Turf.pdf, Apr. 9, 2004).*
BASF (News Release, Mar. 9, 2015).*
Marinez-Esponiza, Apr. 2004.*

* cited by examiner

*Primary Examiner* — Uma Ramachandran

(57) ABSTRACT

The disclosure provides for compositions and including fluopyram. The disclosure further provides for methods of increasing plant yield and reducing plant damage. Soil, seeds, plants, and plant parts treated with compositions described herein are also provided for by the disclosure.

7 Claims, 7 Drawing Sheets

METHODS AND COMPOSITIONS FOR REDUCING *ANGUINA* NEMATODE INFESTATION AND IMPROVING GRASS QUALITY

CROSS REFERENCE TO PRIOR APPLICATIONS

This application claims priority to U.S. 62/189,369 (filed Jul. 7, 2015), the contents of which are incorporated herein by reference in their entirety.

FIELD

The disclosure provides for compositions and methods comprising fluopyram. The disclosure further provides for methods of increasing plant yield and reducing plant damage. Also provided are seeds and plants coated or treated with a composition described herein.

Seeds, soil, plants, and plant parts treated with compositions described herein are also provided for by the disclosure.

BACKGROUND

There is a need to develop compositions and/or methods that are capable of improving plant yield, for example turfgrass, and reducing or controlling the negative influence of pests and associated damage. To this end, the disclosure provides for formulations comprising fluopyram capable of increasing plant yield and reducing damage from pests.

Fluopyram is a fungicide for treating phytopathogenic diseases. The compound is described in U.S. Pat. No. 7,572,818, which is hereby incorporated by reference in its entirety. Fluopyram is currently being used as a foliar fungicide, and it has also shown to be effective as a seed-applied fungicide/nematicide. However, by way of the current disclosure, it is observed that compositions including fluopyram demonstrate unexpected properties on both plant yield and reduction of plant damage.

SUMMARY

In an aspect, the disclosure provides for a method of reducing or controlling damage from a pest in a plant, for example *Anguina* nematode damage in turfgrass, by treating soil, a seed, a plant, and/or a plant part with a composition comprising fluopyram and/or an N-oxide thereof.

In another aspect, the disclosure provides for a method of improving plant yield by treating soil, a seed, a plant, and/or a plant part with a composition comprising fluopyram and/or an N-oxide thereof.

In an aspect, the disclosure provides for a method described herein, wherein a composition comprising fluopyram and/or an N-oxide thereof is applied as a foliar treatment in an application amount from about 100-about 600 g ai/ha, from about 150-about 550 g ai/ha, from about 200-about 525 g ai/ha, or from about 250-about 500 g ai/ha. In an aspect, a composition described herein is applied as a foliar treatment from about 100-about 600 g ai/ha, from about 150 about 550 g ai/ha, from about 200-about 525 g ai/ha, or from about 250-about 500 g ai/ha.

In another aspect, the disclosure provides for a method described herein, for example, a method of reducing or controlling *Anguina* nematode damage, and/or a method of increasing plant yield, wherein soil, a seed, a plant, and/or a plant part is treated with a composition including fluopyram and/or an N-oxide thereof.

In an aspect, nematodes described herein are of the genus *Anguina*.

In another aspect, the disclosure provides for methods of treating nematode infestation and/or plant damage with a composition or method described herein.

Seeds and/or plants treated with compositions described herein are also envisioned.

DETAILED DESCRIPTION

Figure 1:
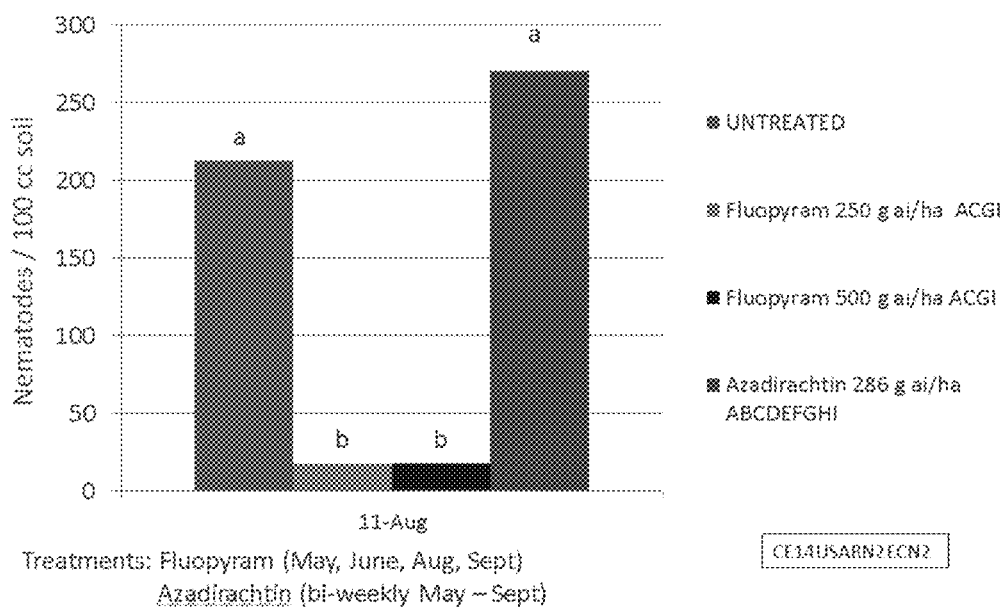
FIG. 1 sets forth comparative numerical representations of *Anguina pacificae* nematodes found in 100 cc untreated soil, 100 cc soil treated with azadirachtin, and 100 cc soil treated with fluopyram at defined concentrations and doses. In the legend provided, each letter (e.g., "A," "B," "C," etc.) represents a two week interval (e.g., AC=4-week interval).

The disclosure provides for compositions comprising fluopyram. The disclosure further provides for fluopyram-based compositions and methods of increasing plant yield and reducing plant damage.

Seeds, soil, plants, and plant parts treated with compositions described herein are also provided for by the disclosure.

Fluopyram has the chemical name N-{2-[3-chloro-5-(trifluoromethyl)-2-pyridinyl]ethyl}-2-(trifluoromethyl) benzamide and a structure as set forth in Formula I:

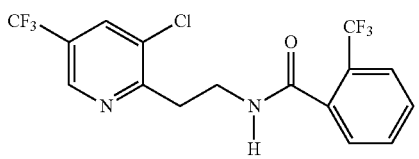

Formula I as well as the N-oxides of the compound thereof. Fluopyram is a fungicide belonging to the chemical class of pyridylethylbenzamides. Fluopyram and its manufacturing process starting from known and commercially available compounds is described in EP-A-1 389 614, which is hereby incorporated by reference in its entirety.

The disclosure provides for a method of reducing plant, root, or plant part damage by treating soil, a seed, plant, root, and/or plant part with a fluopyram-based composition described herein.

In an aspect, the disclosure provides for a method of reducing plant, root, or plant part damage by treating a soil, a seed, plant, root, or plant part with fluopyram.

In a further aspect, the disclosure provides for a method of controlling damage, reducing damage, and/or increasing plant yield comprising a foliar application of a composition comprising, consisting essentially of, or consisting of fluopyram.

In a further aspect, the disclosure provides for use of a composition comprising, consisting essentially of, or consisting of fluopyram in a method of treating nematode infestation.

In conjunction with the present invention "controlling" denotes a preventive, treatment, or curative reduction of the damage in comparison to the untreated plant, more preferably the infestation is essentially repelled, most preferably the infestation is totally suppressed.

In an aspect, the amount of a controlling, damage reducing, or yield increasing composition described herein can be an amount that is effective ("effective amount") to protect seeds, plant parts, or plants against damage or pest infestation and/or increase plant yield.

In yet another aspect, a composition described herein is applied as a foliar treatment in a manner sufficient to convey the desired property, for example, an increased yield or reduction in nematodes.

In an aspect, the composition can also include one or more chelating agents.

In an aspect, a composition described herein, for example fluopyram, can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is liquid solvents, pressurized liquefied gases and/or solid carriers, optionally with the use of surface-active agents, that is emulsifiers and/or dispersants and/or foam formers. If the extender used is water, it is also useful to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants, for example, lignosulphite waste liquors and methylcellulose are suitable.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

Colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc, can also be used.

Plants are understood as meaning, in the present context, all plants and plant populations, such as desired and undesired wild plants or crop plants (including naturally occurring crop plants). Crop plants or crops may be plants which can be obtained by conventional breeding and optimization methods or else by biotechnological and genetic engineering methods or by combinations of these methods, including the transgenic plants and including the plant varieties capable or not capable of being protected by plant breeders' rights.

The disclosure further provides for methods described herein where seeds or plants treated with compositions described herein are selected from grass varieties. In a particular aspect, the disclosure further provides for methods described herein where seeds or plants treated with compositions described herein are selected from species of turfgrass.

In an aspect, a composition described herein is applied to a soil, plant, crop, seed, or plant part thereof in a single application step. In another aspect, a composition described herein is applied to a plant, crop, seed, or plant part thereof in multiple application steps, for example, two, three, four, five or more application steps. In another aspect, the second, third, fourth, or fifth or more application steps may be with the same or different compositions. The methods described herein also provide for an aspect where multiple application steps are excluded.

In another aspect, a composition described herein is applied to a soil, plant, crop, seed, or plant part thereof in one or more application intervals of about 30 minutes, about 1 hour, about 2 hours, about 6 hours, about 8 hours, about 12 hours, about 1 day, about 5 days, about 7 days, about 10 days, about 12 days, about 14 days, about 21 days, about 28 days, about 35 days, about 45 days, about 50 days, or about 56 days.

In an aspect, a composition described herein is applied to a plant, crop, seed, or plant part thereof one or more times during a growing, planting, or harvesting season. In another aspect, a compound or composition described herein is applied to a plant, crop, seed, soil, or plant part thereof in one, two, three, four, or five or more times during a growing, planting, or harvesting season. In another aspect, a compound or composition described herein is applied to a plant, crop, seed, or plant part thereof only one time, no more than two times, or no more than three times during a growing, planting, or harvesting season. In yet another aspect, a compound or composition is applied in a single step to soil.

In another aspect, a compound or composition described herein is applied to soil, plant, crop, seed, or plant part thereof in an application regimen of about every 10 days to about every 50 days, about every 20 days to about every 40 days, or about every 28 days after a first application. In another aspect, a compound or composition described herein is applied to soil in an application regimen of about every 10 days to about every 50 days, about every 20 days to about every 40 days, or about every 28 days after a first application.

Methods described herein can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

In an aspect, plants can be obtained by traditional breeding and optimization methods or by biotechnological and recombinant methods, or combinations of these methods, including the transgenic plants and including the plant varieties which are capable or not capable of being protected by Plant Breeders' Rights.

In another aspect, plant species and plant varieties which are found in the wild or which are obtained by traditional biological breeding methods, such as hybridization or protoplast fusion, and parts of these species and varieties are treated. In a further preferred embodiment, transgenic plants and plant varieties which were obtained by recombinant methods, if appropriate in combination with traditional methods (genetically modified organisms) and their parts are treated.

Plant parts should be understood as meaning all above ground and subsoil parts and organs of plants, such as shoot, leaf, flower, root, leaves, needles, stalks, stems, fruiting bodies, fruits and seeds, tubers and rhizomes. Plant parts also include harvested crops, and also vegetative and generative propagation material, for example cuttings, tubers, rhizomes, slips and seeds.

Seeds, plant parts, and plants may be treated with the described compositions by applying the compounds or compositions directly to the seed, plant part, or plant. In another aspect, the seed, plant part, or plant may be treated indirectly, for example by treating the environment or habitat in which the seed, plant part, or plant is exposed to. Conventional treatment methods may be used to treat the environment or habitat including dipping, spraying, fumigating, chemigating, fogging, scattering, brushing on, shanking or injecting.

According to the invention the treatment of the plants and seeds with a composition described herein, for example fluopyram, can be carried out directly by the customary treatment methods, for example by immersion, spraying, vaporizing, fogging, injecting, dripping, drenching, broadcasting or painting, and seed treatment.

In another aspect, a composition herein treats or reduces nematode infestation.

In yet another aspect, a composition herein treats or reduces *Anguina pacificae* infestation.

In an aspect, a compound or composition described herein is formulated as a foliar composition, a foliar spray, solution, emulsion, coating formulation, non-pesticidal or pesticidal coating formulation, encapsulated formulation, solid, liquid, fertilizer, paste, granule, powder, suspension, or suspension concentrate. In another aspect, a compound or composition described herein may be employed alone or in solid, dispersant, or liquid formulation. In yet another aspect, a compound or composition described herein is formulated as a tank-mix product.

In another aspect, a compound or composition described herein can take any of a variety of dosage forms including, without limitation, suspension concentrates, aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspoemulsion concentrates, soluble concentrates, wettable powders, soluble powders, dusts and granules, water-soluble granules or tablets, water-soluble powders for the treatment of seed, wettable powders, natural products and synthetic substances impregnated with a compound or composition described herein, a net impregnated with a compound or composition described herein, and also microencapsulations in polymeric substances and in coating materials for seed, and also ULV cold-fogging and warm-fogging formulations.

In another aspect, a composition disclosed herein may optionally include one or more additional compounds providing an additional beneficial or otherwise useful effect. Such compounds include, without limitation, an adhesive, a surfactant, a solvent, a wetting agent, an emulsifying agent, a carrier, an adjuvant, a diluent, a dispersing agent an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematicide, a nutritional or horticultural supplement, or any combination thereof. In an aspect, a composition described herein is odor free. In another aspect, the surfactant is Genapol, for example Genapol X-080.

In another aspect, a compositions described herein can be combined with a fertilizer. Examples of fertilizers capable of being used with the compositions and methods described herein include, for example, Urea, Ammonium Nitrate, Ammonium Sulfate, Calcium Nitrate, Diammonium Phosphate, Monoammonium phosphate, Triple Super Phosphate, Potassium Nitrate, Potassium nitrate, nitrate of potash, Potassium Chloride, muriate of potash, di and mono potassium salts of phosphite/phosphonate.

Kit

In another aspect, the disclosure provides for a kit comprising, consisting essentially of, or consisting of any of the compounds or compositions disclosed herein. In an aspect, the kit includes any of the compounds or compositions described in Examples 1-3, FIGS. 1-6, or Tables 1-7. In another aspect, the kit provides for the compositions described in Examples 1-3, FIGS. 1-6, or Tables 1-7 applied in a manner that is consistent with the methodology of these examples and figures. In another aspect, the kit provides instructions or guidance regarding the use of the compositions or methods described herein.

In an aspect, the kit includes instructions describing the methodology described herein. In another aspect, the kit includes instructions describing the methodology set forth in any of Examples 1-3, FIGS. 1-6, or Tables 1-7. In an aspect, the instructions are included with the kit, separate from the kit, in the kit, or are included on the kit packaging.

The following examples serve to illustrate certain aspects of the disclosure and are not intended to limit the disclosure.

What is claimed is:

1. A method of reducing or controlling nematode damage in a plant comprising treating soil, a seed, a plant, and/or a plant part with a composition comprising fluopyram and/or an N-oxide thereof.

2. The method according to claim 1, wherein said nematode is of the genus *Anguina*.

3. The method according to either claim 1 or claim 2, wherein said nematode is *Anguina pacificae*.

4. The method according to any of claims 1-3, wherein said composition is applied as a foliar treatment.

5. The method according to any of claims 1-4, wherein said composition is applied as a foliar treatment to turfgrass.

6. The method according to claim 5, wherein said turfgrass is *Poa annua*.

7. The method according to any of claims 1-6, wherein said composition is applied in an application amount from about 100 g ai/ha to about 600 g ai/ha.

8. The method according to claim 6, wherein said composition is applied in an application amount from about 150 g ai/ha to about 550 g ai/ha.

9. The method according to claim 6, wherein said composition is applied in an application amount from about 200 g ai/ha to about 525 g ai/ha.

10. The method according to any of claims 1-9, wherein said composition is applied from about every 10 days to about every 50 days after a first application of said composition.

11. The method of claim 10, wherein said composition is applied from about every 20 days to about every 40 days after a first application.

12. The method of claim 11, wherein said composition is applied about every 28 days after a first application 13. Use of a composition comprising fluopyram and/or an N-oxide thereof wherein said composition reduces or controls nematode damage in a plant when treating soil, a seed, a plant, and/or a plant part with said composition.

14. The use according to claim 13, wherein said nematode is of the genus *Anguina*.

15. The use according to either claim 13 or 14, wherein said nematode is *Anguina pacificae*.

16. The use according to any of claims 13-15, wherein said composition is applied as a foliar treatment.

17. The use according to claim 16, wherein said composition is applied as a foliar treatment to turfgrass.

18. The use according to claim 17, wherein said turfgrass is *Poa annua*.

EXAMPLES

Example 1

Example 1 describes effects of various treatments on nematode population on a *Poa annua* green at Pebble Beach.

Trials are kept free of any pests that can interfere or impact and nematode evaluations and yields.

A *Poa annua* green is treated by spraying the active ingredient on foliage and waiting at least three hours before irrigating into the thatch/mat layer for upward movement into the stem region (just above the crown) where the nematode resides. One or more applications can be made in 2-8 weeks. The interval may be longer if control has not declined, or treatments are to be applied in different seasons (e.g., spring and fall).

In FIG. 1, a *Poa annua* green is evaluated and counts of nematodes per 100 cc soil are taken 87 days after anthesis (DAA). The first column represents nematode count at 87 DAA in an untreated sample of turfgrass. The second column represents nematode count at 87 DAA in turfgrass treated with 250 g ai/ha fluopyram at 4-week intervals. The third column represents nematode count at 87 DAA in turfgrass treated with 500 g ai/ha fluopyram at 4-week intervals. The fourth column represents nematode count at 87 DAA in turfgrass treated with 286 g ai/ha azadirachtin applied bi-weekly to the soil. FIG. 1 corresponds to Table 1, below.

TABLE 1

Nematode count, Pebble Beach, 87 DAA

| Treatment | Nematodes/100 cc soil |
| --- | --- |
| Untreated | 212.5 |
| 250 g ai/ha fluopyram | 17.5 |
| 500 g ai/ha fluopyram | 17.5 |
| 286 g ai/ha azadirachtin | 270 |

Figure 2:
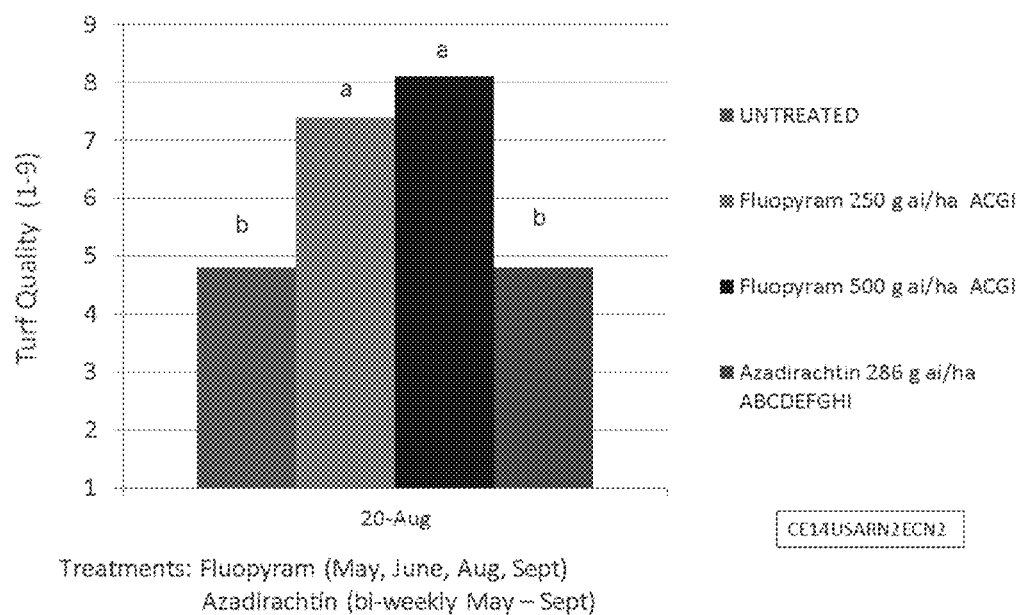
FIG. 2 sets forth comparative turf quality evaluations of *Poa annua* turfgrass treated with fluopyram at defined concentrations and doses. In the legend provided, each letter (e.g., "A," "B," "C," etc.) represents a two week interval (e.g., AC=4-week interval).

In FIG. 2, turf quality of a *Poa annua* green is evaluated 96 DAA. The first column represents turf quality at 96 DAA in an untreated sample of turfgrass. The second column represents turf quality at 96 DAA in turfgrass treated with 250 g ai/ha fluopyram at 4-week intervals. The third column represents turf quality at 96 DAA in turfgrass treated with 500 g ai/ha fluopyram at 4-week intervals. The fourth column represents turf quality at 96 DAA in turfgrass treated with 286 g ai/ha azadirachtin applied bi-weekly to the soil. FIG. 2 corresponds to Table 2, below.

TABLE 2

Turf quality, Pebble Beach, 96 DAA

| Treatment | Turf Quality[w] |
| --- | --- |
| Untreated | 4.8 |
| 250 g ai/ha fluopyram | 7.4 |
| 500 g ai/ha fluopyram | 8.1 |
| 286 g ai/ha azadirachtin | 4.8 |

[w]Turfgrass quality is on a 1-9 scale (9 = best, 6 = acceptable) based on color, density, and uniformity.

A Crop Circle ACS-430 active crop canopy sensor (Holland Scientific, Inc.) provided classic vegetation index data (RVI=Ratio Vegetation Indices; NDVI=Normalized difference vegetative index) from the turf canopy. Unlike passive radiometric light sensors, the Crop Circle ACS-430 is not limited by ambient lighting conditions and measurements were made by day due to its unique light source technology. Information produced by the sensor can be utilized to quantify the impact of nutrients, water, disease or other growing conditions on the turf plant. The ratio vegetation index (RVI) is formed by dividing the near infra-red irradiance by the red irradiance. Study plots were scanned at intervals to collect this quantitative data. The normalized difference vegetative index (NDVI) is calculated as follows:

$$NDVI = \frac{(NIR - VIS)}{(NIR + VIS)}$$

where VIS and NIR stand for the spectral reflectance measurements acquired in the visible (red) and near-infrared regions, respectively.

Figure 3:
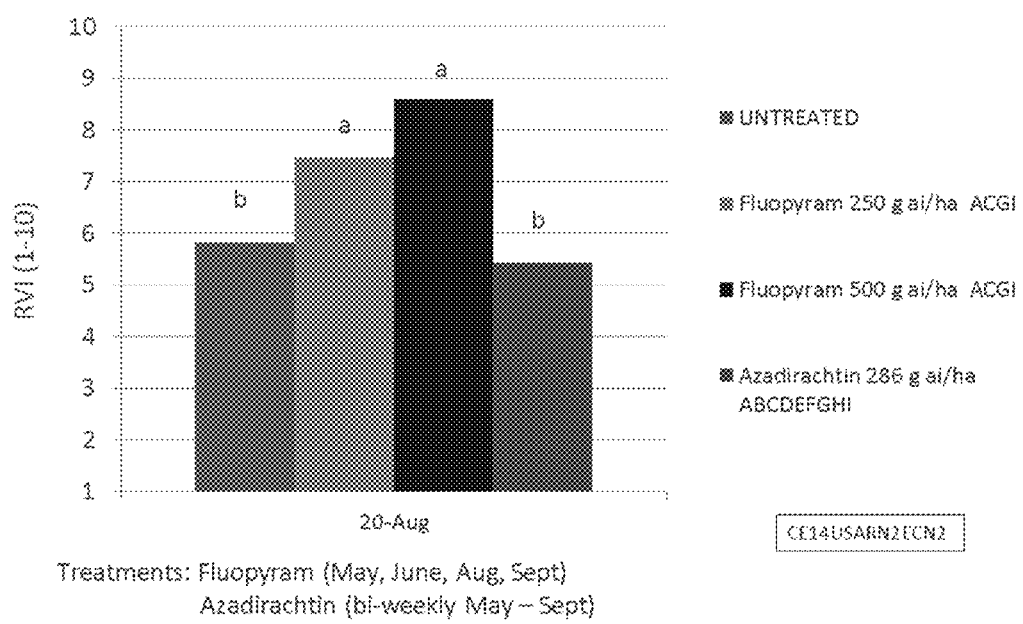
FIG. 3 sets forth comparative RVI measurements of *Poa annua* turfgrass treated with fluopyram at defined concentrations and doses. In the legend provided, each letter (e.g., "A," "B," "C," etc.) represents a two week interval (e.g., AC=4-week interval).

Crop circle assays of sampled turfgrass were taken after treatment with the invention compositions listed in Tables 3 and 4. FIG. 3 demonstrates the ratio vegetative index ("RVI") for the evaluated *Poa annua* grass, and FIG. 4 demonstrates the normalized difference vegetative index ("NDVI") for the evaluated *Poa annua* grass. Using RVI and NDVI as exemplary indicators, FIGS. 3 and 4 demonstrate that treatment of turfgrass with fluopyram positively enhanced vegetative index when averaged over the course of the study as compared to the untreated control.

In FIG. 3, RVI of a *Poa annua* green is evaluated 96 DAA. The first column represents RVI at 96 DAA in an untreated sample of turfgrass. The second column represents RVI at 96 DAA in turfgrass treated with 250 g ai/ha fluopyram at 4-week intervals. The third column represents RVI at 96 DAA in turfgrass treated with 500 g ai/ha fluopyram at 4-week intervals. The fourth column represents RVI at 96 DAA in turfgrass treated with 286 g ai/ha azadirachtin applied bi-weekly to the soil. FIG. 3 corresponds to Table 3, below.

TABLE 3

RVI, Pebble Beach, 96 DAA

| Treatment | RVI[x] |
| --- | --- |
| Untreated | 5.830 |
| 250 g ai/ha fluopyram | 7.475 |
| 500 g ai/ha fluopyram | 8.598 |
| 286 g ai/ha azadirachtin | 5.425 |

[x]RVI = Ratio Vegetation Index (near infra-red irradiance divided by red irradiance).

Figure 4:
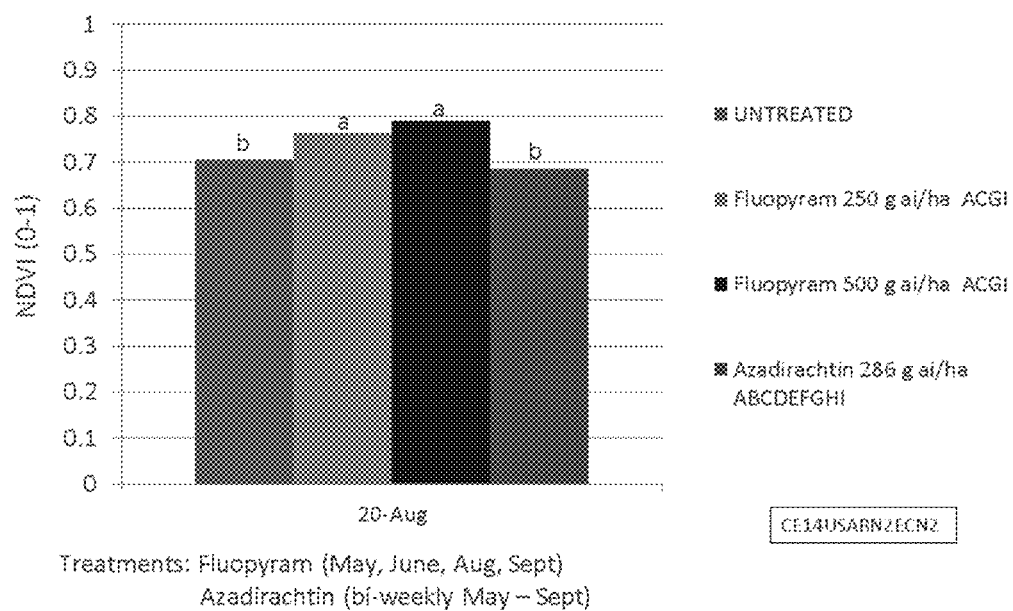
FIG. 4 sets forth comparative NDVI measurements of *Poa annua* turfgrass treated with fluopyram at defined concentrations and doses. In the legend provided, each letter (e.g., "A," "B," "C," etc.) represents a two week interval (e.g., AC=4-week interval).

In FIG. 4, NDVI of a *Poa annua* green is evaluated 96 DAA. The first column represents NDVI at 96 DAA in an untreated sample of turfgrass. The second column represents NDVI at 96 DAA in turfgrass treated with 250 g ai/ha fluopyram at 4-week intervals. The third column represents NDVI at 96 DAA in turfgrass treated with 500 g ai/ha fluopyram at 4-week intervals. The fourth column represents NDVI at 96 DAA in turfgrass treated with 286 g ai/ha azadirachtin applied bi-weekly to the soil. FIG. 4 corresponds to Table 4, below.

TABLE 4

NDVI, Pebble Beach, 96 DAA

| Treatment | NDVI[y] |
| --- | --- |
| Untreated | 0.7064 |
| 250 g ai/ha fluopyram | 0.7634 |
| 500 g ai/ha fluopyram | 0.7908 |
| 286 g ai/ha azadirachtin | 0.6865 |

[y]NDVI = Normalized Difference Vegetation Index = NIR/(NIR + VIS).

Example 2

Example 2 describes effects of various treatments on nematode population on a *Poa annua* green at Pebble Beach.

Trials are kept free of any pests that can interfere or impact and nematode evaluations and yields.

A *Poa annua* green is treated by spraying the active ingredient on foliage and waiting at least three hours before irrigating into the thatch/mat layer for upward movement into the stem region (just above the crown) where the nematode resides. One or more applications can be made in 2-8 weeks. The interval may be longer if control has not declined, or treatments are to be applied in different seasons (e.g., spring and fall).

Figure 5:
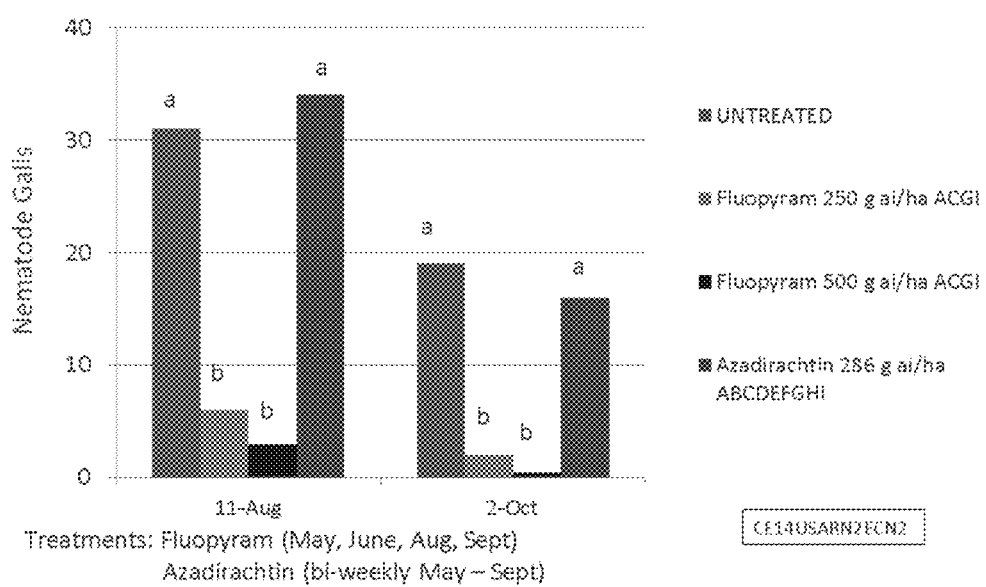
FIG. 5 sets forth comparative numerical representations of *Anguina pacificae* nematodes galls found in 100 cc untreated soil, 100 cc soil treated with azadirachtin, and 100 cc soil treated with fluopyram at defined concentrations and doses. In the legend provided, each letter (e.g., "A," "B," "C," etc.) represents a two week interval (e.g., AC=4-week interval).

In FIG. 5, a *Poa annua* green is evaluated and counts of nematode galls per 100 cc soil are taken 87 and 139 days after anthesis (DAA). The first and fifth columns represent nematode gall count at 87 and 139 DAA, respectively, in an untreated sample of turfgrass. The second and sixth columns represent nematode gall count at 87 and 139 DAA, respectively, in turfgrass treated with 250 g ai/ha fluopyram at 4-week intervals. The third and seventh columns represent nematode gall count at 87 and 139 DAA, respectively, in turfgrass treated with 500 g ai/ha fluopyram at 4-week intervals. The fourth and eighth columns represent nematode gall count at 87 and 139 DAA, respectively, in turfgrass treated with 286 g ai/ha azadirachtin applied bi-weekly to the soil. FIG. 5 corresponds to Table 5 (87 DAA) and Table 6 (139 DAA), below.

TABLE 5

Nematode galls, Pebble Beach, 87 DAA

| Treatment | Nematode galls/100 cc soil |
| --- | --- |
| Untreated | 31 |
| 250 g ai/ha fluopyram | 6 |
| 500 g ai/ha fluopyram | 3 |
| 286 g ai/ha azadirachtin | 34 |

TABLE 6

Nematode galls, Pebble Beach, 139 DAA

| Treatment | Nematode galls/100 cc soil |
| --- | --- |
| Untreated | 19 |
| 250 g ai/ha fluopyram | 2 |
| 500 g ai/ha fluopyram | 0.5 |
| 286 g ai/ha azadirachtin | 16 |

Example 3

Example 3 describes effects of various treatments on nematode population on a *Poa annua* green at The Links at Spanish Bay.

Trials are kept free of any pests that can interfere or impact and nematode evaluations and yields.

A *Poa annua* green is treated by spraying the active ingredient on foliage and waiting at least three hours before irrigating into the thatch/mat layer for upward movement into the stem region (just above the crown) where the nematode resides. One or more applications can be made in 2-8 weeks. The interval may be longer if control has not declined, or treatments are to be applied in different seasons (e.g., spring and fall).

Figure 6:
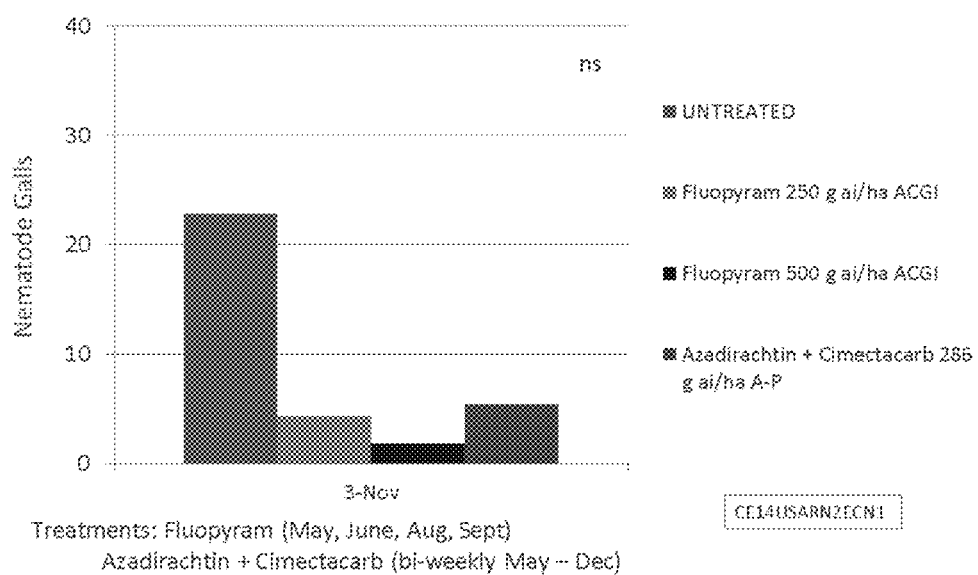
FIG. 6 sets forth comparative numerical representations of *Anguina pacificae* nematode galls found in 100 cc untreated soil, 100 cc soil treated with azadirachtin+cimectacarb, and 100 cc soil treated with fluopyram at defined concentrations and doses. In the legend provided, each letter (e.g., "A," "B," "C," etc.) represents a two week interval (e.g., AC=4-week interval).

In FIG. 6, a *Poa annua* green is evaluated and counts of nematode galls per 100 cc soil are taken 171 days after anthesis (DAA). The first column represents nematode count at 171 DAA in an untreated sample of turfgrass. The second column represents nematode count at 171 DAA in turfgrass treated with 250 g ai/ha fluopyram at 4-week intervals. The third column represents nematode count at 171 DAA in turfgrass treated with 500 g ai/ha fluopyram at 4-week intervals. The fourth column represents nematode count at 171 DAA in turfgrass treated with 286 g ai/ha azadirachtin and cimectacarb applied bi-weekly to the soil. FIG. 6 corresponds to Table 7, below.

TABLE 7

Links at Spanish Bay, 171 DAA

| Treatment | Nematode galls/100 cc soil |
| --- | --- |
| Untreated | 22.8 |
| 250 g ai/ha fluopyram | 4.3 |
| 500 g ai/ha fluopyram | 1.8 |
| 286 g ai/ha azadirachtin + cimectacarb | 5.5 |

Figure 7:
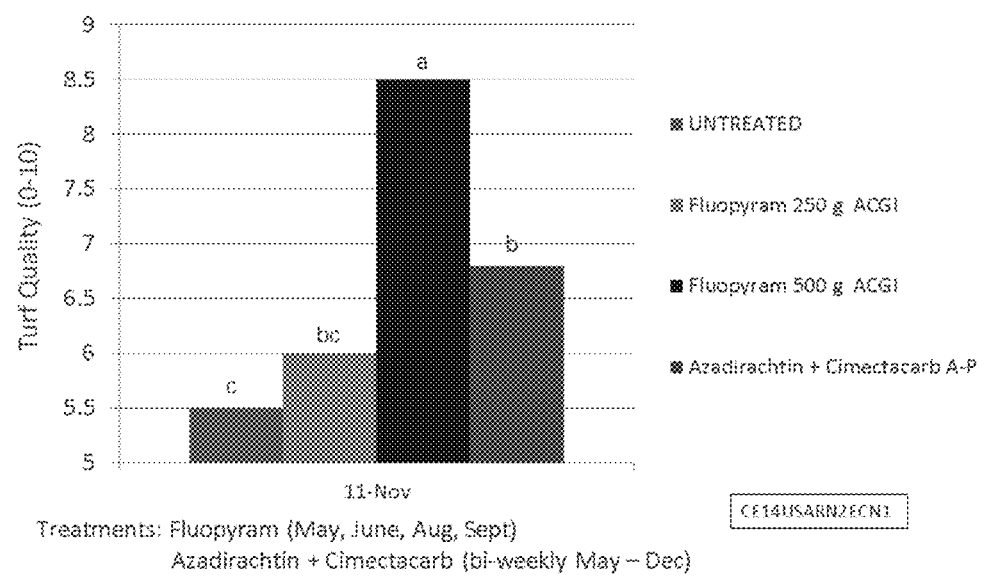
FIG. 7 sets forth comparative turf quality evaluations of *Poa annua* turfgrass treated with fluopyram at defined concentrations and doses. In the legend provided, each letter (e.g., "A," "B," "C," etc.) represents a two week interval (e.g., AC=4-week interval).

In FIG. 7, turf quality of a *Poa annua* green is evaluated 179 DAA. The first column represents turf quality at 179 DAA in an untreated sample of turfgrass. The second column represents turf quality at 179 DAA in turfgrass treated with 250 g ai/ha fluopyram at 4-week intervals. The third column represents turf quality at 179 DAA in turfgrass treated with 500 g ai/ha fluopyram at 4-week intervals. The fourth column represents turf quality at 179 DAA in turfgrass treated with 286 g ai/ha azadirachtin applied bi-weekly to the soil. FIG. 7 corresponds to Table 8, below.

TABLE 8

Turf quality, Links at Spanish Bay, 179 DAA

| Treatment | Turf Quality[z] |
| --- | --- |
| Untreated | 5.5 |
| 250 g ai/ha fluopyram | 6.0 |
| 500 g ai/ha fluopyram | 8.5 |
| 286 g ai/ha azadirachtin + cimectacarb | 6.8 |

[z]Turfgrass quality is on a 0-10 scale (10 = best) based on color, density, and uniformity.

The invention claimed is:

1. A method of reducing or controlling nematode damage caused by nematodes of the genus *Anguina* in turfgrass comprising treating the turfgrass by a foliar treatment of a composition comprising fluopyram and/or an N-oxide thereof, to thereby reduce or control nematode damage, wherein fluopyram is the sole active component in the composition, wherein said composition is applied in an application amount of about 100 g fluopyram/ha to about 600 g fluopyram/ha, wherein said nematode is *Anguina pacificae* and wherein said turfgrass is *Poa annua*.

2. The method according to claim 1, wherein said composition is applied in an application amount from about 150 g fluopyram/ha to about 550 g fluopyram/ha.

3. The method according to claim 1, wherein said composition is applied in an application amount from about 200 g fluopyram/ha to about 525 g fluopyram/ha.

4. The method according to claim 1, wherein said composition is applied from about every 10 days to about every 50 days after a first application of said composition.

5. The method of claim 4, wherein said composition is applied from about every 20 days to about every 40 days after a first application.

6. The method of claim 5, wherein said composition is applied about every 28 days after a first application.

7. The method of claim 1, wherein the nematodes are infesting the turfgrass before treatment.

* * * * *